(12) United States Patent
Youssef et al.

(10) Patent No.: US 10,705,068 B2
(45) Date of Patent: Jul. 7, 2020

(54) SYSTEM AND METHOD FOR MEASURING A FLOW PROPERTY OF A FLUID IN A POROUS MEDIUM

(71) Applicant: IFP Energies nouvelles, Rueil-Malmaison (FR)

(72) Inventors: Souhail Youssef, Montreuil (FR); Yannick Peysson, Rueil Malmaison (FR); Herve Deschamps, Noisy le Roi (FR)

(73) Assignee: IFP ENERGIES NOUVELLES, Rueil-Malmaison (FR)

(*) Notice: Subject to any disclaimer, the term of this patent is extended or adjusted under 35 U.S.C. 154(b) by 2 days.

(21) Appl. No.: 16/070,540

(22) PCT Filed: Dec. 15, 2016

(86) PCT No.: PCT/EP2016/081139
§ 371 (c)(1),
(2) Date: Jul. 17, 2018

(87) PCT Pub. No.: WO2017/129312
PCT Pub. Date: Aug. 3, 2017

(65) Prior Publication Data
US 2019/0056376 A1    Feb. 21, 2019

(30) Foreign Application Priority Data

Jan. 29, 2016  (FR) .................................... 16 50711

(51) Int. Cl.
*G01N 23/00*  (2006.01)
*G01N 33/24*  (2006.01)
*G01N 23/04*  (2018.01)
*G01N 15/08*  (2006.01)
*G01N 11/04*  (2006.01)
*G01N 11/00*  (2006.01)

(52) U.S. Cl.
CPC .......... *G01N 33/241* (2013.01); *G01N 11/04* (2013.01); *G01N 15/082* (2013.01); *G01N 23/04* (2013.01); *G01N 2011/006* (2013.01); *G01N 2015/0846* (2013.01)

(58) Field of Classification Search
CPC ..................................................... G01N 23/04
See application file for complete search history.

(56) References Cited

U.S. PATENT DOCUMENTS 5,109,398 A    4/1992  Hunt et al.
5,164,672 A *  11/1992  Gilliland .............. G01N 33/241
                                                    250/255

FOREIGN PATENT DOCUMENTS

WO    2008/132132 A1    11/2008
WO    2012/164090 A1    12/2012

OTHER PUBLICATIONS

International Search Report for PCT/EP2016/081139, dated Feb. 16, 2017; English translation submitted herewith (7 pgs.)
(Continued)

*Primary Examiner* — Dani Fox
(74) *Attorney, Agent, or Firm* — Fitch, Even, Tabin & Flannery, L.L.P.

(57) ABSTRACT

The invention relates to a system and to a method for measuring at least one flow property of at least one fluid in a porous medium. The measurement system (1) comprises at least one cell (2), means (7) for injecting fluid(s) into the cell and X-ray radiography means (4, 5).

18 Claims, 3 Drawing Sheets

(56) References Cited

OTHER PUBLICATIONS

Rezki Oughanem et al: "Pore-Scale to Core-Scale Study of Capillary Desaturation Curves Using Multi-Scale 3D Imaging", IOR 2013—From Fundamental Science to Deployment, Sep. 19, 2013 (Sep. 19, 2013), pp. 16-19, XP055150813, DOI: 10.3997/2214-4609.20142615, the whole document.

* cited by examiner

SYSTEM AND METHOD FOR MEASURING A FLOW PROPERTY OF A FLUID IN A POROUS MEDIUM

CROSS-REFERENCE TO RELATED APPLICATIONS

This application is a U.S. national phase application filed under 35 U.S.C. § 371 of International Application No. PCT/EP2016/081139, filed Dec. 15, 2016, designating the United States, which claims priority from French Patent Application No. 16/50.711, filed Jan. 29, 2016, which are hereby incorporated herein by reference in their entirety.

FIELD OF THE INVENTION

The present invention relates to the field of flow property measurement of a fluid in a porous medium, notably a porous medium from an underground formation. Measurements can be used notably for determining the residual oil saturation of an underground formation, in particular during the exploration and exploitation of hydrocarbon wells, and especially for enhanced oil recovery (EOR).

BACKGROUND OF THE INVENTION

It is estimated today that, for all of the active oil reservoirs, 60%-65% of the oil in place remains trapped. Various mechanisms are responsible for this trapping, for example, geological heterogeneity generates non-homogeneous displacement of the oil at reservoir scale. However, even at local scale, the presence of an interfacial tension between water and oil leads to capillary trapping of the oil phase in the centre of the pores in the case of water-wet rocks. This trapping can represent up to 50% of the oil in place. Water-wet reservoirs constitute approximately half of the world's reservoirs.

Mobilizing the residual oil contained in the matrix under preferential water wettability conditions therefore is a real challenge. However, using surfactants injected in aqueous phase can lead to a significant capillary trapping decrease. Surfactants have the property of reducing considerably this tension or even of nearly cancelling it out. The use of surfactant additives has been successfully tested on sandstones in the 1980s and it is experiencing renewed interest. Surfactant enhanced oil (hydrocarbons) recovery methods represent a strong potential as they allow to untrap a significant amount of oil blocked in the pores of rocks.

To characterize capillary untrapping, it is necessary to perform measurements of relative fluid flow properties in the porous medium. Currently, the methods used require several weeks to obtain this fluid flow characterization. Indeed, it is currently necessary to prepare rock samples having a sufficient pore volume for the fluids produced and collected at the pore volume outlet to have a sufficient volume for characterizing the properties of the medium (typically several milliliters). Thus, typical sample sizes are of the order of 5 cm in diameter and 10 cm in length. The samples are then initially saturated with water, drained with oil and finally subjected to waterflooding so as to obtain the residual oil saturation. Injection of a volume of an ASP (Alkaline-Surfactant-Polymer) formulation and subsequently a final waterflooding sequence are then performed. At the end of the sequence, the residual oil saturation is deduced from the total volume of oil produced at the porous medium outlet.

Besides, in other technical fields, it may be interesting to rapidly characterize the flow of a fluid in a porous medium, notably a porous medium consisting of a polymer.

The invention relates to a system and to a method for measuring at least one flow property of at least one fluid in a porous medium. The measurement system comprises at least one cell, means for injecting fluid(s) into the cell and X-ray radiography means. Using X-ray radiography means in a cell into which a fluid can be injected allows measurements to be performed rapidly and in real time.

SUMMARY OF THE INVENTION

The invention relates to a system for measuring at least one flow property of at least one fluid in a porous medium. Said measurement system comprises at least one cell containing said porous medium, means for injecting said fluid into said cell and X-ray radiography means including a source and a detector, said X-ray radiography means being suited to perform a plurality of X-rays upon injection of said fluid.

According to an embodiment of the invention, said measurement system comprises means for controlling said injection means.

According to a variant embodiment, said measurement system comprises means for collecting and/or analyzing said X-rays obtained by said detector.

Advantageously, said cell has a substantially cylindrical shape.

Preferably, the diameter of said cell substantially ranges between 2 mm and 5 cm, preferably between 5 mm and 2 cm.

According to an implementation of the invention, said injection means comprise a plurality of fluids to be injected into said cell, simultaneously or sequentially.

Advantageously, said injection means comprise at least one pump, at least one valve and at least one pressure detector.

According to an embodiment, said fluid is selected from among an aqueous phase and an oil phase.

According to a characteristic, at least one aqueous phase comprises at least one additive, notably a surfactant.

According to a design, said measurement system comprises means for positioning said cell.

Furthermore, the invention relates to a method for measuring at least one flow property of at least one fluid in a porous medium, wherein said measurements are performed by means of said measurement system according to one of the above characteristics.

Advantageously, said flow properties are selected from among the average saturation of said fluid and/or the saturation profile of said fluid and/or the pressure difference of said fluid within said sample.

Preferably, a plurality of X-rays are performed upon injection of said fluid.

According to an embodiment, a plurality of X-rays are performed at regular intervals substantially ranging between 0.1 and 5 seconds.

According to an embodiment of the invention, a residual saturation curve is plotted as a function of the flood capillary number by means of said measurements.

According to a variant embodiment, the X-ray radiography measurements are performed by means of said measurement system while carrying out the following injection steps in said cell:

a) injecting oil at least at two different flow rates;
b) injecting water at least at two different flow rates; and c) injecting an aqueous phase comprising at least one additive at least at two different flow rates.

BRIEF DESCRIPTION OF THE FIGURES

Other features and advantages of the system and of the method according to the invention will be clear from reading the description hereafter, given by way of non-limitative example, with reference to the accompanying figures wherein.

DETAILED DESCRIPTION OF THE INVENTION

Figure 1:
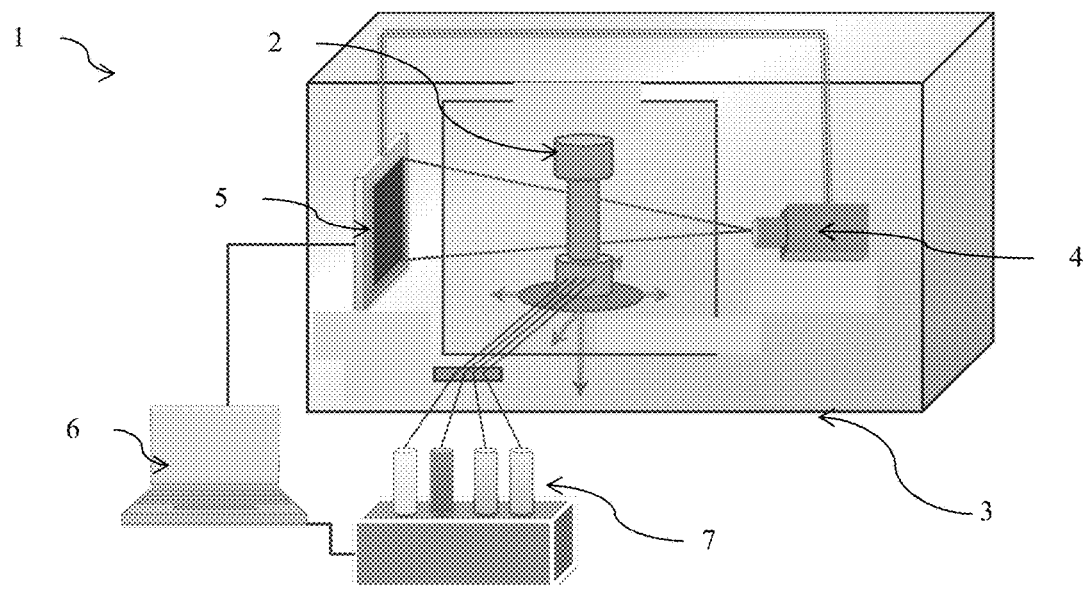
FIG. 1 illustrates a measurement system according to an embodiment of the invention.

The present invention relates to a system for measuring at least one flow property of at least one fluid in a porous medium. The flow properties can notably be the average saturation of the fluid and/or the saturation profile of the fluid and/or the pressure difference of the fluid in the porous medium, etc. The flow properties can depend on the operating parameters and on the flow rates of each fluid. The fluid can be of any type, it can notably comprise an aqueous phase, an oil phase. . . . When the fluid comprises an aqueous phase, it can further comprise at least one additive, a surfactant for example. Surfactants exhibit the property of decreasing very significantly the interfacial tension between water and oil, or even of nearly cancelling it out. The porous medium can be of any type, it can notably consist of a rock sample taken from an underground formation, or it can be a porous polymer. In cases where the porous medium is a rock, it is possible to characterize the fluid(s) flows in the underground formation.

The measurement system according to the invention comprises:
  at least one cell suited to contain the porous medium, the cell can be referred to as sample holder and the measurement system can comprise several cells so as to perform simultaneous measurements,
  means for injecting the fluid into the cell; the injection means are suited to circulate at least one fluid in the cell, for example the injection means can comprise at least one fluid tank, at least one line connecting the tank to the cell, at least one pump, at least one valve and at least one pressure detector,
  X-ray radiography means; the X-ray radiography means comprise at least one X-ray source and an X-ray detector, preferably a flat-panel detector, the cell being positioned between the source and the detector; the radiography means are capable of performing a plurality of X-rays upon injection of at least one fluid in the cell.

The X-ray radiography means allow to perform measurements of the fluid flow property in the porous medium contained in the cell. Indeed, through calibration, it is possible to connect the grey level of the X-ray image obtained to the saturation in the porous medium. A previous image can therefore be performed with the sample saturated with at least one fluid to be injected in the porous medium. Thus, it is possible to have "reference" X-rays, to be compared with the X-rays made during injection. For example, in the case of a measurement relative to a rock sample, a first X-ray can be performed for a water-saturated sample, then a second X-ray can be performed for an oil-saturated sample. Using a plurality of X-rays also allows fast measurement (of the order of one hour, to be compared with the few weeks required for current measurements) in real time.

For safety reasons, the radiography means and the cell can be inside an X-ray protection cabin, while the other components of the measurement system, notably the fluid injection means, can be outside the protection cabin.

Furthermore, the measurement system can comprise the following elements, alone or in combination:
  means for controlling the injection means, for example these control means are suited to control at least one pump, at least one valve and at least one flowmeter, etc.; the control means can include a computer system,
  means for collecting and/or analyzing X-rays obtained by the radiography means detector; the collection and/or analysis means allow to store and/or to analyze the measurements obtained with the X-rays, for example, the collection and/or analysis means can comprise a computer system; in this case, the collection and/or analysis means can also be used as measurement display means, and the collection and/or analysis means can notably connect the grey level of each X-ray image to the saturation in the porous medium,
  cell shifting means; the shifting means can be suited to shift the cell through translational motions in two horizontal directions and in a vertical direction; it is thus possible to adapt the measurement system to different cell dimensions.

In cases where the measurement system comprises both means for controlling the injection means and X-ray collection and/or analysis means, a single computer system can fulfil these two functions.

According to an embodiment of the invention, the cell of the measurement system can have a substantially cylindrical shape. Preferably, the cell has small dimensions (it is then referred to as mini-sample) in relation to the conventional sizes used for oil saturation measurements. These conventional dimensions are of the order of 5 cm in diameter and 10 cm in length. According to a possible design of the cell, the diameter of the cell (or the diameter in which the cell is inscribed when it does not have a cylindrical shape) substantially ranges between 2 mm and 3 cm, preferably between 5 mm and 2 cm. For example, the diameter of the cell can be approximately 1 cm. The length (height) of the cell can range between 5 and 50 mm, and it can for example be approximately 20 mm. The reduced dimensions of the cell in relation to the samples conventionally used allow measurements to be performed more rapidly, notably because the injection times can be shorter. Thanks to shorter experiment durations, the mini-samples also allow to carry out several experiments and to study the desired results statistically.

According to an embodiment of the invention, the cell can be intended to operate at temperatures close to 150° C. and at pressures close to 150 bars.

The means for injecting the fluid into the cell can be suited to inject a single fluid. Alternatively, the injection means can be suited to inject a plurality, for example 2 to 5 fluids, into the cell. In this case, injection of the various fluids can be performed sequentially or simultaneously. The possibility of injecting different fluids allows to provide particular injection sequences in order to determine certain properties of the flow in the sample. For example, when studying a surfactant for an EOR method, it is feasible to provide three fluids to be injected: water, oil and an aqueous phase comprising a surfactant.

Furthermore, the means for injecting the fluid into the cell can comprise means for adjusting the rate of injection of the fluid into the cell, a flowmeter for example, in order to perform flow rate-dependent measurements.

Besides, the fluid injection means can comprise at least one pressure regulator for regulating the pressure of the fluid injected into the cell.

According to an embodiment of the invention, the X-ray radiography means can be suited to perform X-rays at regular intervals during the injection of fluid (s). The regular interval can range between 0.1 and 5 seconds, and it can be 1 second for example. Thus, performing X-rays at regular intervals allows regular monitoring of the flows in the cell, which enables real-time monitoring of the flows in the sample.

FIG. 1 schematically shows, by way of non-limitative example, a measurement system according to an embodiment of the invention. Measurement system 1 comprises a cell 2 containing a rock sample (not shown), or any other porous medium. Cell 2 is arranged in an X-ray protection cabin 3. Cabin 3 also comprises X-ray radiography means including an X-ray source 4 and an X-ray detector 5. Cell 2 is placed on a support that can be shifted along three axes (schematically shown by arrows). Measurement system 1 also comprises means 7 for injecting the fluid into the cell. Injection means 7 are provided with four fluids. Injection means 7 are connected to the cell by four lines. Injection means 7 are arranged outside X-ray protection cabin 3. Moreover, measurement system 1 comprises a computer system 6. Computer system 6 is connected to detector 5 and to injection means 7. Computer system 6 is used for controlling injection means 7 and the collection and analysis means intended for the X-rays obtained by detector 5. Computer system 6 is arranged outside protection cabin 3.

The present invention also relates to a method for measuring at least one flow property of at least one fluid in a porous medium. The measurement method according to the invention is based on the use of the measurement system according to the invention.

The method according to the invention can comprise the following steps;
placing a porous medium to be analyzed in the cell of the measurement system;
injecting one or more fluids into the cell using the fluid injection means of the measurement system;
during injection, performing a plurality of X-rays with the radiography means of the measurement system; and
determining at least one flow property by means of the X-rays.

The method according to the invention allows to measure at least one of the following properties: the average saturation of a fluid injected into the porous medium, the saturation profile of a fluid injected into the porous medium, the pressure difference of the fluid injected into the porous medium, etc.

Furthermore, these values allow to measure a residual saturation (oil saturation for example) for various flood (injection) flow rates of an aqueous phase containing a surfactant. It is then possible to plot a residual saturation curve as a function of the flood capillary number. The curve showing the evolution of the residual oil saturation as a function of the capillary number is referred to as CDC (Capillary Desaturation Curve). It can represent the amount of oil producible by an EOR process through injection of an aqueous composition comprising at least one surfactant. The CDC therefore plays an important role in an EOR process. This curve notably depends on the nature of the rock.

Thus, the method according to the invention can be used within the context of an enhanced oil recovery (EOR) process wherein the method according to the invention is used with the measurement system according to the invention to determine the formulation of the composition (water and at least one additive, including a surfactant) injected into the underground formation. In this case, the porous medium used corresponds to a rock sample taken from the underground formation where the EOR process is implemented.

According to an embodiment of the invention, the X-ray radiography means can be suited to perform X-rays at regular intervals during the fluid injection(s). The regular interval can range between 0.1 and 5 seconds, and it can be 1 second for example. Thus, performing X-rays at regular intervals allows regular monitoring of the flows in the cell, which enables real-time monitoring of the flows in the sample.

According to an embodiment, for which the relevance of injecting a surfactant into a rock is analyzed, the method according to the invention can comprise the following injection sequence:
oil drainage with several different flow rates, i.e. oil injection in order to drain the water present in the sample, for example at three different flow rates,
waterflooding at several different flow rates, i.e. water injection to remove the excess oil, at two different flow rates for example; waterflooding can be carried out at a very low or even zero flow rate, in this case the water sweeps the porous medium only by capillary forces, which is referred to as spontaneous imbibition,
injection of an aqueous phase comprising a surfactant at different increasing flow rates, eight different flow rates for example, until total oil desaturation.

During these four steps, X-rays of the cell are performed. Furthermore, this sequence can comprise the following steps:
injecting a volume of water, and
washing and cleaning the sample.

According to an alternative, the method according to the invention can comprise simultaneous injection of water and oil for different flow rates. These common injections notably allow the relative permeability to be measured.

EXAMPLE

The system and the method according to the invention are implemented during a sequence aimed to characterize the evolution of the residual oil saturation during various water and surfactant flooding operations at different flow rates.

A 10 mm diameter and 19 mm long sandstone sample is used in one of the cells. The sample is initially 100% saturated with water. The injection sequence performed by the measurement system illustrated in FIG. 1 is as follows:
E1: oil drainage at three different flow rates,
E2: spontaneous imbibition, E3: waterflooding at two given flow rates, and E4: injection of surfactant in aqueous phase at eight increasing flow rates until total oil desaturation.

Figure 2:
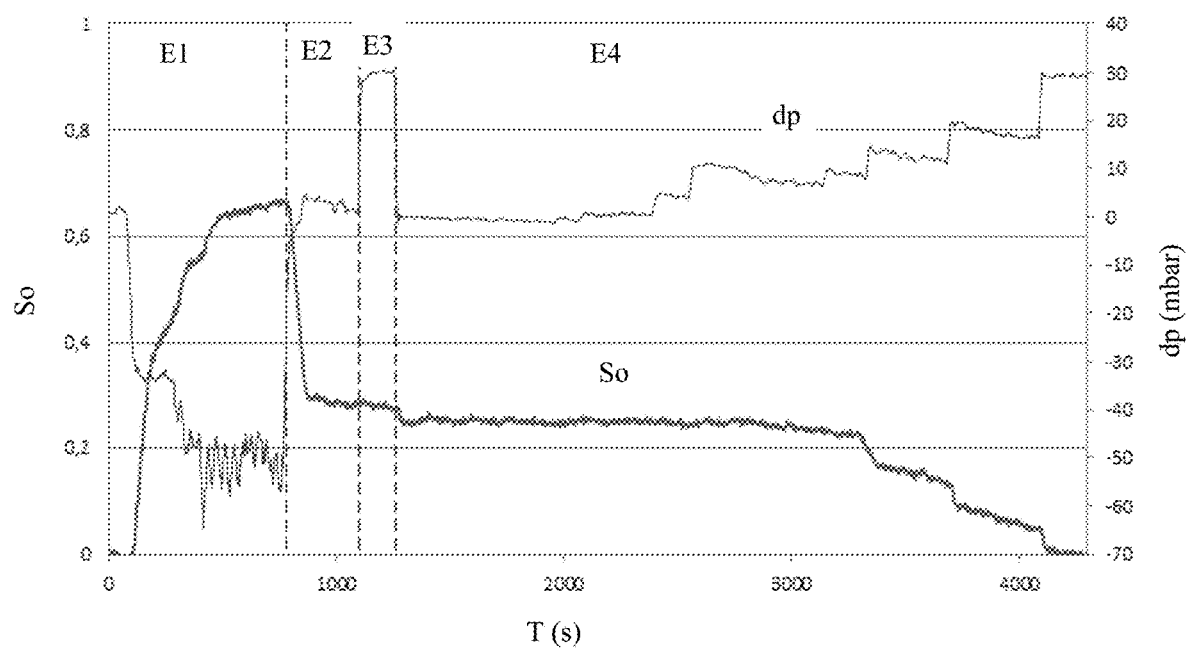
FIG. 2 illustrates the average oil saturation and the pressure difference for an example of a method according to the invention.

During the experiment, an X-ray is recorded every second, thus allowing to obtain, after calibration, both the average oil saturation and the saturation profile along the sample. The pressure difference over time is also measured. The average saturation So and the pressure difference dp (mbar) as a function of time T (s) are shown in FIG. 2 for injection sequence E1 to E4. The whole cycle is completed in 4000 seconds, i.e. a little over an hour. It is noted that the injection of surfactant in aqueous phase allows all of the oil present in the sample to be extracted: at the end of the sequence, So=0. Simultaneously, the pressure difference increases in the sample.

Figure 3:
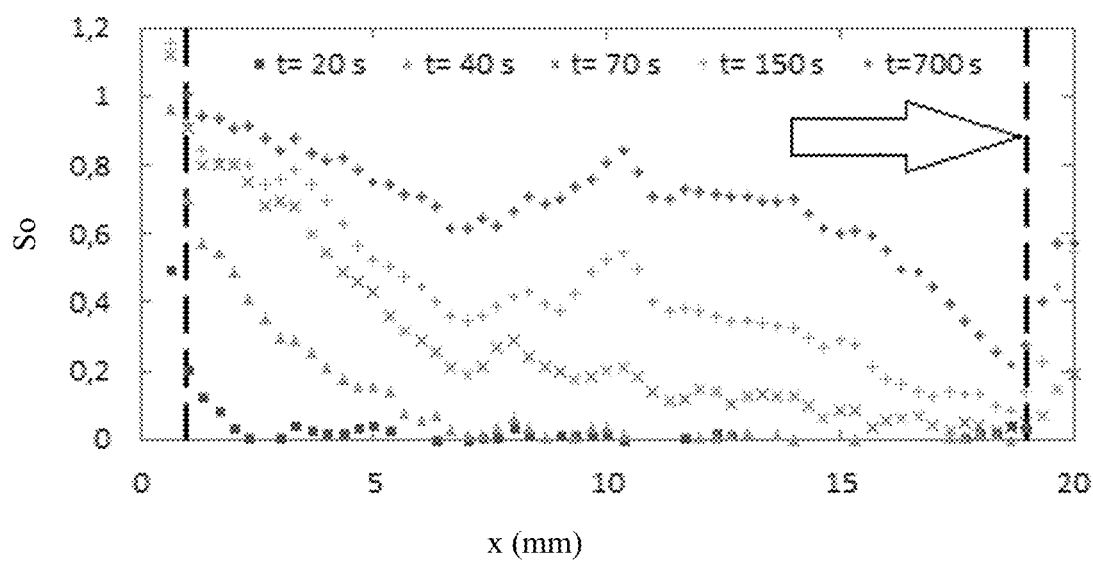
FIG. 3 illustrates the oil saturation profile along the sample during the drainage phase at several times for the example of FIG. 2.
Figure 4:
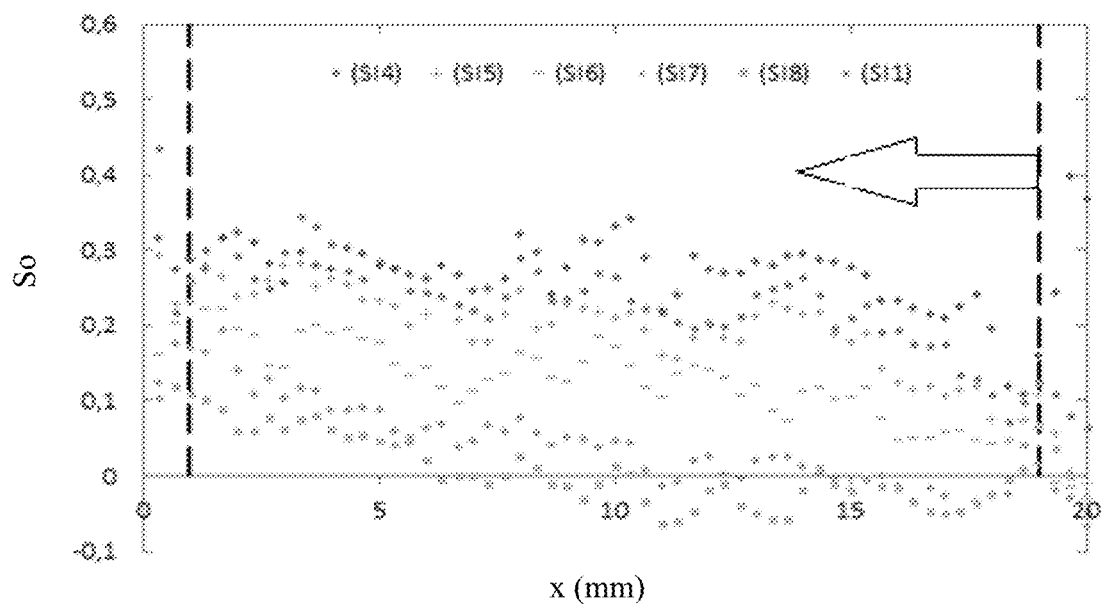
FIG. 4 illustrates the oil saturation profile along the sample during the surfactant flooding phase at several flow rates for the example of FIG. 2.

The saturation profiles for each sequence are also obtained from each measured X-ray. The processing performed is a moving average along the image. Added to calibration, one can obtain the oil saturation along the sample every second. FIG. 3 and FIG. 4 show two examples of oil saturation profiles So as a function of the depth of the sample x (mm), obtained during drainage phase E1 and during the surfactant flooding phase E4. In these figures, the boundaries of the samples are symbolized by discontinuous vertical lines and the direction of injection is shown by an arrow. FIG. 3 shows the evolution of saturation So at different times: t=20 s, t=40 s, t=70 s, t=150 s and t=700 s. As expected, the oil saturation increases during the drainage phase. FIG. 4 shows the evolution of saturation So at the end of various water and surfactant injection sequences at different flow rates denoted by SI4, SI5, SI6, SI7, SI8 and SI11 (SI=Surfactant Injection), with SI4: 0.16 $cm^3$/min, SI5: 0.25 $cm^3$/min, SI6: 0.5 $cm^3$/min, SI7: 1 $cm^3$/min, SI8: 2 $cm^3$/min and SI11: 0.02 $cm^3$/min.

Figure 5:
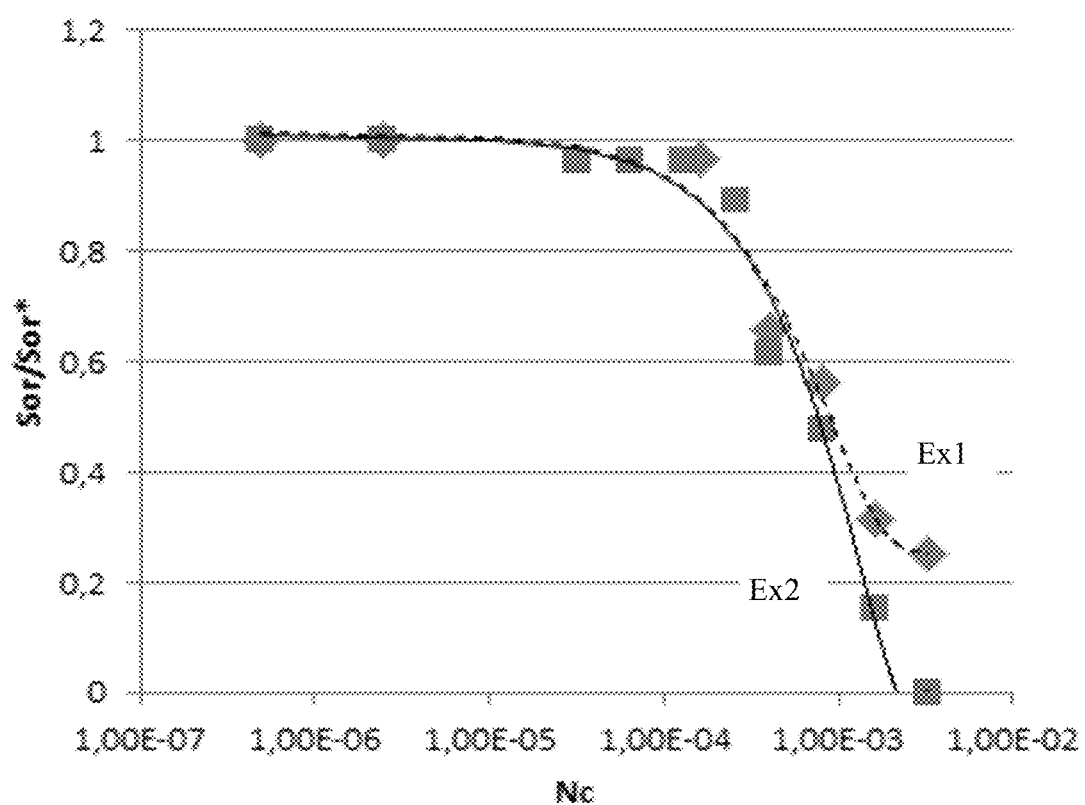
FIG. 5 shows the residual saturation measured with the system as a function of the flood capillary number for two rock types for the example of FIG. 2.

The profiles obtained allow to measure the residual saturation for each water and surfactant flooding stage E4. It is then possible to plot the residual saturation curve Sor/Sor* (with Sor the residual saturation and Sor* the normalized residual saturation) as a function of the flood capillary number Nc (FIG. 5), which is an important datum for any EOR survey. Capillary number Nc is the ratio between the average flood flow velocity times the water viscosity divided by the interfacial tension between the water/surfactant system and the oil. In FIG. 5, two curves are obtained for two different sandstone samples with the same experimental sequence: Bentheimer sandstone and Clashach sandstone.

Thus, within about one hour, it is possible to obtain a precise CDC curve, unlike conventional methods that may require several weeks.

The invention claimed is:

1. A system for measuring at least one flow property of at least one fluid in a porous medium, wherein the system comprises at least one cell containing the porous medium, means for injecting the at least one fluid into the at least one cell, and X-ray radiography means including a source and a detector, the X-ray radiography means being suited to perform a plurality of X-rays upon injection of the at least one fluid, wherein the plurality of X-rays are performed at regular intervals substantially ranging between 0.1 and 5 seconds.

2. A system as claimed in claim 1, wherein the system further comprises means for controlling the means for injecting.

3. A system as claimed in claim 1, wherein the system further comprises means for collecting and/or analyzing the X-rays obtained by the detector.

4. A system as claimed in claim 1, wherein the at least one cell has a substantially cylindrical shape.

5. A system as claimed in claim 4, wherein the diameter of the at least one cell substantially ranges between 2 mm and 5 cm.

6. A system as claimed in claim 1, wherein the means for injecting comprises a plurality of fluids to be injected into the at least one cell, simultaneously or sequentially.

7. A system as claimed in claim 4, wherein the diameter of the at least one cell substantially ranges between 5 mm and 2 cm.

8. A system as claimed in claim 1, wherein the means for injecting comprises at least one pump, at least one valve and at least one pressure detector.

9. A system as claimed in claim 1, wherein the at least one fluid is selected from among an aqueous phase and an oil phase.

10. A system as claimed in claim 9, wherein at least one aqueous phase comprises at least one additive.

11. A system as claimed in claim 10, wherein the at least one additive comprises a surfactant.

12. A system as claimed in claim 1, wherein the system further comprises means for positioning the at least one cell.

13. A method for measuring at least one flow property of at least one fluid in a porous medium, the method comprising performing measurements on the porous medium using a system comprising at least one cell containing the porous medium, means for injecting the at least one fluid into the at least one cell, and X-ray radiography means including a source and a detector, the X-ray radiography means being suited to perform a plurality of X-rays upon injection of the at least one fluid, wherein the plurality of X-rays are performed at regular intervals substantially ranging between 0.1 and 5 seconds.

14. A method as claimed in claim 13, wherein the at least one flow property comprises at least one selected from among the average saturation of the at least one fluid, the saturation profile of the at least one fluid, and the pressure difference of the at least one fluid within the sample.

15. A method as claimed in claim 13, wherein the plurality of X-rays are performed upon injection of the at least one fluid.

16. A method as claimed in claim 13, further comprising plotting a residual saturation curve as a function of the flood capillary number by means of the measurements.

17. A method as claimed in claim 13, wherein the X-ray radiography measurements are performed by means of the system while carrying out the following injection steps in the at least one cell:

a) injecting oil at least at two different flow rates;
    b) injecting water at least at two different flow rates; and
    c) injecting an aqueous phase comprising at least one additive at least at two different flow rates.

18. A system for measuring at least one flow property of at least one fluid in a porous medium, the system comprising:

at least one cell containing the porous medium,
    at least one injector configured to inject the at least one fluid into the at least one cell,
    an X-ray source configured to emit X-rays at regular intervals during injection of the at least one fluid into the at least one cell, and
    an X-ray detector configured to detect the X-rays emitted from the X-ray source after the X-rays pass through the at least one cell.

* * * * *